(12) United States Patent
Garrett et al.

(10) Patent No.: US 9,884,421 B2
(45) Date of Patent: Feb. 6, 2018

(54) NON-ANTHROPOMORPHIC HIP JOINT LOCATIONS FOR EXOSKELETONS

(71) Applicant: Ekso Bionics, Inc., Richmond, CA (US)

(72) Inventors: Scott Garrett, Berkeley, CA (US); Robert Moore, Union City, CA (US); Tim Swift, Clovis, CA (US); Kurt Amundson, Berkeley, CA (US); Russdon Angold, American Canyon, CA (US)

(73) Assignee: Ekso Bionics, Inc., Richmond, CA (US)

( * ) Notice: Subject to any disclaimer, the term of this patent is extended or adjusted under 35 U.S.C. 154(b) by 147 days.

(21) Appl. No.: 14/776,310

(22) PCT Filed: Mar. 12, 2014

(86) PCT No.: PCT/US2014/024403
§ 371 (c)(1),
(2) Date: Sep. 14, 2015

(87) PCT Pub. No.: WO2014/159608
PCT Pub. Date: Oct. 2, 2014

(65) Prior Publication Data
US 2016/0031076 A1    Feb. 4, 2016

Related U.S. Application Data

(60) Provisional application No. 61/781,376, filed on Mar. 14, 2013.

(51) Int. Cl.
*B25J 9/00*    (2006.01)
*A61F 5/01*    (2006.01)
(Continued)

(52) U.S. Cl.
CPC ........... *B25J 9/0006* (2013.01); *A61F 5/0102* (2013.01); *A61H 1/024* (2013.01); *A61H 1/0244* (2013.01);
(Continued)

(58) Field of Classification Search
CPC ........ B25J 9/0006; B25J 9/1633; B25J 17/00; A61H 1/024; A61H 1/0244; A61H 3/00;
(Continued)

(56) References Cited

U.S. PATENT DOCUMENTS 7,553,266 B2 * 6/2009 Abdoli-Eramaki ..... A61F 5/026
482/124
8,002,719 B2    8/2011 Ashihara et al.
(Continued)

FOREIGN PATENT DOCUMENTS

| CN | 101803966 | 8/2010 |
| GB | 2278041 | 11/1994 |
| WO | WO 2011/127421 | 10/2011 |

*Primary Examiner* — Anita M King
(74) *Attorney, Agent, or Firm* — Diederiks & Whitelaw, PLC

(57) ABSTRACT

An exoskeleton device provides for selectively adjusting an exoskeleton hip pivot/pivot position in the sagittal plane relative to the position of the hip pivot of a wearer of the exoskeleton. The exoskeleton hip pivots/pivot positions can be shifted forward or rearward relative to the hip pivots of the wearer and can either be automatically actuated by an exoskeleton control system or manually adjusted by the exoskeleton wearer. The invention particularly allows for differential hip placement in order to compensate for changing load or actuation conditions.

20 Claims, 6 Drawing Sheets

(51) Int. Cl.
*A61H 3/00* (2006.01)
*A61H 1/02* (2006.01)
*B25J 9/16* (2006.01)
*B25J 17/00* (2006.01)

(52) U.S. Cl.
CPC .............. *A61H 3/00* (2013.01); *B25J 9/1633* (2013.01); *B25J 17/00* (2013.01); *A61H 2201/0192* (2013.01); *Y10S 901/01* (2013.01)

(58) Field of Classification Search
CPC ........... A61H 2201/0192; Y10S 901/01; A61F 5/0102
USPC ........................................................ 248/550
See application file for complete search history.

(56) References Cited

U.S. PATENT DOCUMENTS

| | | | |
|---|---|---|---|
| 8,388,559 B2 | 3/2013 | Kudoh | |
| 8,474,672 B1 * | 7/2013 | Keith | B25J 9/0006 224/576 |
| 8,591,438 B2 | 11/2013 | Ikeuchi | |
| 8,702,632 B2 * | 4/2014 | Han | A61F 5/0102 601/23 |
| 9,492,300 B2 * | 11/2016 | Bujold | A61F 5/0102 |
| 9,504,623 B2 * | 11/2016 | Angold | B25J 9/0006 |
| 9,539,466 B1 * | 1/2017 | Schoner | A63B 23/0476 |
| 9,604,369 B2 * | 3/2017 | Angold | A61H 1/0244 |
| 9,782,892 B2 * | 10/2017 | Angold | B25J 9/0006 |
| 2005/0279796 A1 | 12/2005 | Chu et al. | |
| 2006/0276728 A1 * | 12/2006 | Ashihara | A61F 5/0102 601/5 |
| 2007/0123997 A1 | 5/2007 | Herr et al. | |
| 2011/0266323 A1 | 11/2011 | Kazerooni et al. | |
| 2013/0303950 A1 | 11/2013 | Angold et al. | |
| 2015/0001269 A1 * | 1/2015 | Sacksteder | F16M 13/04 224/576 |
| 2015/0016923 A1 * | 1/2015 | Brown | A61F 5/01 414/1 |
| 2015/0321341 A1 * | 11/2015 | Smith | A61H 1/0237 623/27 |
| 2015/0351995 A1 * | 12/2015 | Zoss | A61H 1/024 623/32 |
| 2016/0229065 A1 * | 8/2016 | Angold | A61H 1/0244 |

\* cited by examiner

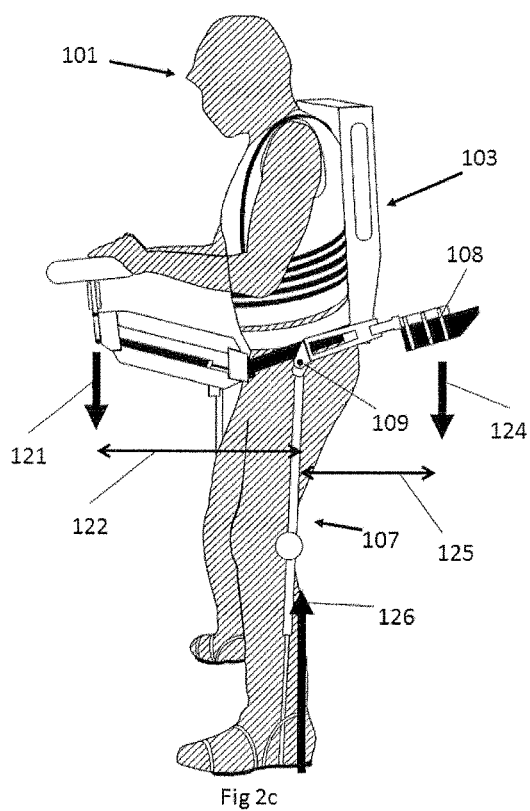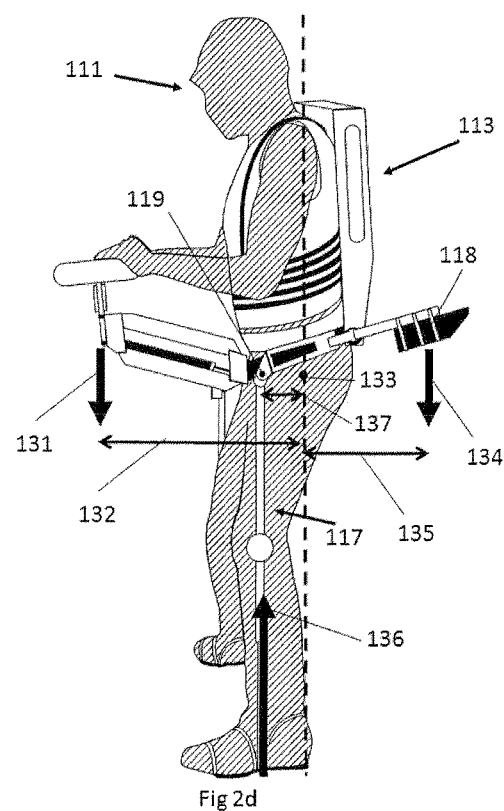

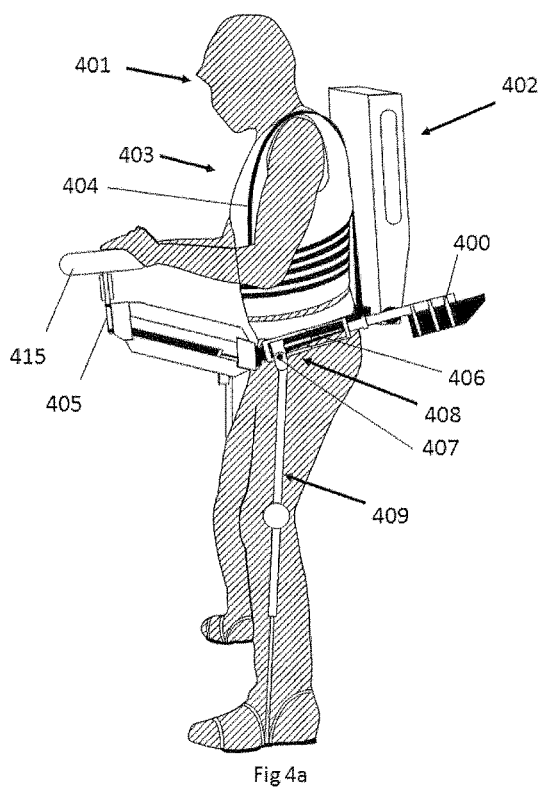
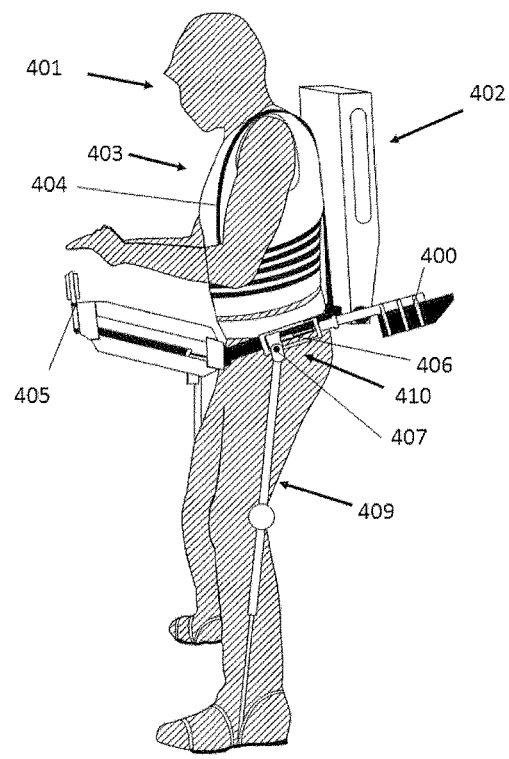
Fig 4a
Fig 4b

NON-ANTHROPOMORPHIC HIP JOINT LOCATIONS FOR EXOSKELETONS

CROSS-REFERENCE TO RELATED APPLICATION

The present application represents a National Stage application of PCT/US2014/024403 entitled "Non-Anthropomorphic Hip Joint Locations for Exoskeletons" filed Mar. 12, 2014, pending, which claims the benefit of U.S. Provisional Application Ser. No. 61/781,376 filed Mar. 14, 2013 entitled "Non-Anthropomorphic Hip Joint Locations for Exoskeletons" filed Mar. 14, 2013.

STATEMENT REGARDING FEDERALLY SPONSORED RESEARCH OR DEVELOPMENT

This invention was made with U.S. government support under NSF Grant #0956801. The U.S. government has certain rights in the invention.

BACKGROUND OF THE INVENTION

The present invention relates to a device and method that augments a user's strength and aids in the prevention of injury during the performance of certain strength-requiring tasks. More particularly, the present invention relates to a device suitable for use by a person engaging in heavy tool use or weight bearing tasks, comprising a set of artificial limbs and related control systems that potentiate improved function of the person's appendages for activities including, but not limited to, greater strength and endurance in the wearer's arms, or allowing for more weight to be carried by the wearer while walking.

Wearable exoskeletons have been designed for medical, commercial and military applications. Medical exoskeletons are designed to help restore a user's mobility. Commercial and military exoskeletons help prevent injury and augment the user's strength. Commercial exoskeletons are used to alleviate loads supported by workers during their labor, thereby preventing worker injuries and increasing their stamina and strength.

Initial testing has been performed using an exoskeleton outfitted with a tool holding arm that supports the weight of the tool. These devices reduce user fatigue by providing tool holding assistance. The tool holding arm transfers the vertical force required to hold the tool through the legs of the exoskeleton rather than through the user's arms. One problem with this exoskeleton use is that the tool is held in front of the exoskeleton's legs. This produces a forward falling torque about the exoskeleton hip joint that must be resisted by the user. Users tend to lean back excessively to compensate for this forward torque which places unwanted loads on the user's body.

In order to reduce this load on the user's body, a counteracting torque must be applied at the hip joint. Using a spring to create this torque will generate too great a torque in the swing phase (unless the spring can be disengaged, and such mechanisms are generally heavy and complex). Although this can be avoided with an actuated hip joint, such a design requires constant power consumption while standing, requiring heavy batteries and negating the advantage. For an exoskeleton with non-actuated hips, a weight must be installed behind the user to provide the necessary torque to counteract the weight of the tool and minimize the load felt by the user. A counter torque can be produced with a range of weights and moment arms: lighter weights require longer moment arms and heavier weights require shorter moment arms. These, however, are undesirable because heavier counter weights will make the exoskeleton heavier and harder to move, while longer moment arms reduce maneuverability in what is often a confined work environment.

For at least these reasons, there exists a need to develop a device and method that allow for a reduction in the forward hip torque in an exoskeleton with a tool-holding arm.

SUMMARY OF THE INVENTION

It is an object of the present invention to provide a novel device and method that causes a reduction of forward torque at the hip joint of a tool holding exoskeleton.

It is an additional object of the present invention to provide a novel device and method that causes a reduction of backwards torque at the hip joint of exoskeletons where the load is behind the user, as in the case where the exoskeleton is used to bear the load of a backpack.

It is an additional object of the present invention to provide a novel device and method that allows the forward or backwards torque at the hip of an exoskeleton to be reduced in an adjustable way, allowing for exoskeleton wearer or exoskeleton control system selection torque reduction for either forwards or backwards torque at the hip joint of an exoskeleton, as required or preferred for various movements of tasks.

The invention disclosed herein comprises devices and methods for reducing either forwards or backwards torque at the hip joint of an exoskeleton by modifying the placement of the hip joint of the exoskeleton relative to exoskeleton weight distribution in the sagittal plane. These modifications to exoskeleton hip placement build upon current exoskeleton technology to enable an exoskeleton system to shift various other exoskeleton parameters including, but not limited to, lessened exoskeleton wearer hip torque input, lessened exoskeleton hip actuator torque input, greater tool weight, greater load weight, lessened rear counterweight mass, shorter moment arms, or some combination of these parameters.

The primary embodiment of this invention comprises an exoskeleton device with a mechanical design that misaligns the exoskeleton hip pivot forward in the sagittal plane relative to the exoskeleton wearer's hip pivot. For the application of a tool holding exoskeleton, this mechanical design reduces the counter torque required to hold a tool in place.

A second embodiment of this invention comprises an exoskeleton device with a mechanical design that misaligns the exoskeleton hip pivot rearward in the sagittal plane relative to the exoskeleton wearer's hip pivot. For the application of a backpack load bearing exoskeleton, this mechanical design reduces the counter torque required to hold a load in place.

A third embodiment of this invention comprises an exoskeleton device with a mechanical design that adjustably alters the exoskeleton hip pivot position in the sagittal plane relative to the position of the exoskeleton wearer's hip pivot. This device, which can either be automatically actuated by the exoskeleton control system or manually adjusted by the exoskeleton wearer, allows for differential hip placement in order to compensate for changing load or actuation conditions. For the application of a tool holding exoskeleton, this mechanical design reduces the counter torque required to hold a tool in place while standing by shifting the hip pivot forward, and increases exoskeleton mobility while walking or maneuvering by shifting the hip pivot rearward.

Additional objects, features and advantages of the invention will become more fully apparent from the following description of specific embodiments of the invention when taken in conjunction with the drawings.

BRIEF DESCRIPTION OF THE FIGURES

FIG. 2c is a schematic side view of a worker wearing a tool-holding exoskeleton showing the forces exerted by the tool, counterweight, and ground, as well as the distances between the downward forces and the hip of the exoskeleton wearer.

FIG. 2d is a representation of the first embodiment showing a schematic side view of a worker wearing a tool-holding exoskeleton with forward shifted hips showing the forces exerted by the tool, counterweight, and ground, as well as the distances between these vertical forces and the hip of the exoskeleton relative hip of the exoskeleton wearer.

FIG. 4a is a drawing representing a third embodiment that shows a schematic side view of a worker wearing a tool-holding exoskeleton that has adjustable exoskeleton hip positioning, with the adjustable exoskeleton hips being shown in the forward position.

FIG. 4b is a drawing representing the third embodiment that shows a schematic side view of a worker wearing a tool-holding exoskeleton that has adjustable exoskeleton hip positioning, with the adjustable exoskeleton hips being shown in the rearward position.

DETAILED DESCRIPTION OF THE INVENTION

The present invention is used in conjunction with a powered orthotic device that augments a user's strength and aids in the prevention of injury during the performance of certain strength-requiring tasks. More particularly, the present invention relates to a device and method suitable for use by a person engaging in heavy tool use or weight bearing tasks, comprising a motorized system of braces and related control systems that potentiate improved function of the appendages for activities including, but not limited to, greater strength and endurance in the wears arms, or more weight to be carried while walking.

Figures 1A, 1B:
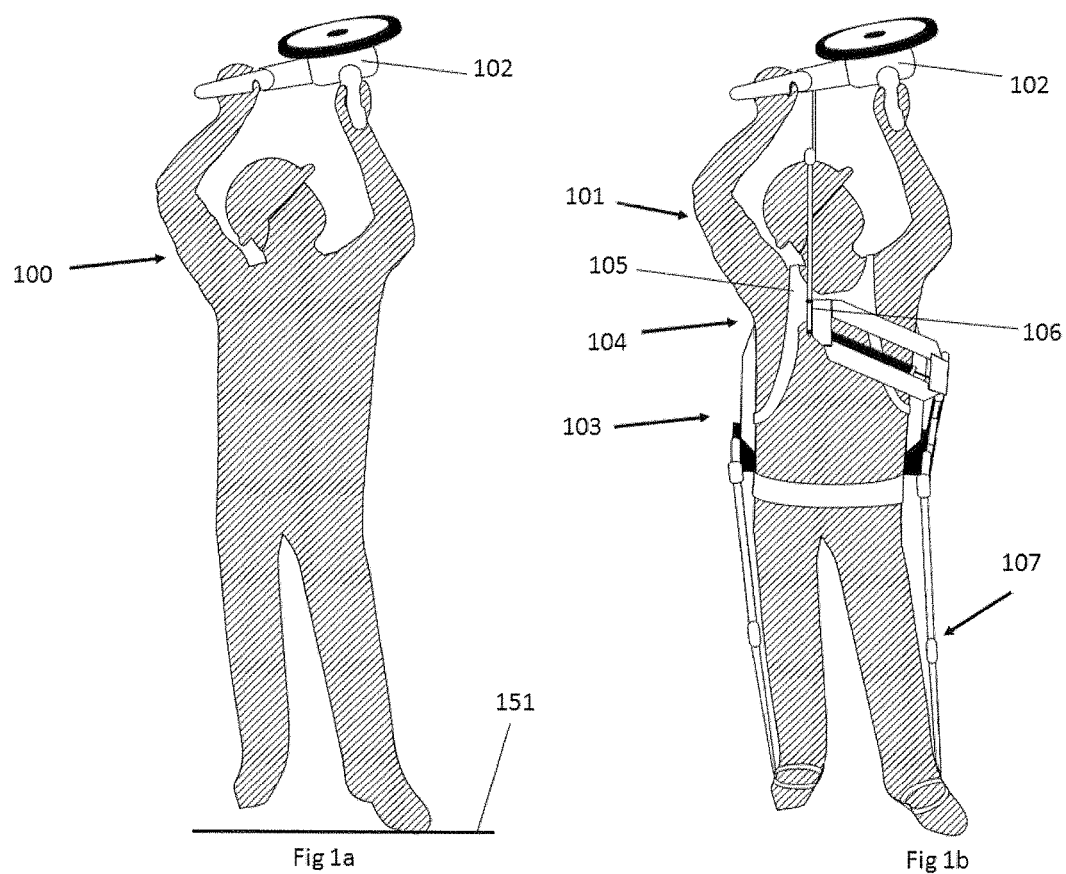
FIG. 1a is a drawing showing a front view of a worker who is holding a tool over his head in accordance with the prior art.
FIG. 1b is a drawing showing a front view of a worker wearing a tool-holding exoskeleton while holding a tool over their head in accordance with the invention.

As shown in the known arrangement of FIG. 1a, a worker 100 holds a heavy tool 102 (shown in this illustration as a heavy grinder) above his head while performing a work function standing on support surface 151 (generally omitted in other figures for clarity). The weight of heavy tool 102 is supported entirely by worker 100 during the course of this work function. FIG. 1b shows worker 101 wearing an exoskeleton 103, which is attached to torso 104 of worker 101 by person-exoskeleton strapping 105, in accordance with the invention. Commercial exoskeleton 103 is equipped with tool holding arm 106 which supports the weight of heavy tool 102. During the course of the work function shown in FIG. 1b, tool holding arm 106 supports some or all of the weight of heavy tool 102, with this weight being transferred to exoskeleton 103 which is supported by exoskeleton legs 107 configured to be coupled to lower limbs of the user and rest on a support surface during a stance phase. As the specific design of the exoskeleton leg below the hip is not an object of this invention, and because the object of this invention applies across a range of exoskeleton leg designs, the design of the legs will not be further detailed. In this way, exoskeleton 103 supports the weight of the heavy tool 102 and allows the worker 101 to perform this task for significantly longer periods of time with less fatigue, resulting in greater worker productivity and lessened risk of worker injury, relative to worker 100 in FIG. 1a.

Testing was performed using an exoskeleton outfitted with a tool holding arm that supports the weight of the tool as set forth above. This device reduced user fatigue by providing tool holding assistance in which the tool holding arm transfers the vertical force required to hold the tool through the legs of the exoskeleton rather than through the user's arms. One problem with this application is that the tool is held in front of the exoskeleton's legs. This produces a forward falling torque about the exoskeleton hip joint that must be resisted by the exoskeleton wearer. Wearers tends to lean back excessively to compensate for this forward torque which places unwanted loads on the wearer's body. In order to reduce this load on the wearer's body, a counteracting torque must be applied at the exoskeleton hip joint. Although this can be done with an actuated exoskeleton hip joint, such a design requires constant power consumption while standing. For an exoskeleton with non-actuated hips, a weight must be installed behind the user to provide the necessary torque to counteract the weight of the tool and minimize the load felt by the user. A counter torque can be produced with a range of weights and moment arms: lighter weights require longer moment arms and heavier weights require shorter moment arms. These, however, are undesirable because heavier counter weights will make the exoskeleton heavier and harder to move, and longer moment arms reduce maneuverability in what is often a confined work environment.

The primary embodiment of this invention comprises an exoskeleton device with a mechanical design that misaligns the exoskeleton hip pivot forward in the sagittal plane relative to the exoskeleton wearer's hip pivot. For the application of a tool holding exoskeleton, this mechanical design reduces the counter torque required to hold a tool in place.

Traditional exoskeleton hip pivots are aligned as closely as possible to the user hip so as to not limit the user range of motion and minimize the relative motion between the exoskeleton and the user. However, it has been found to be acceptable to violate this rule in applications where a great range of motion of the hip is not frequently required. One such application is a tool holding exoskeleton in which the user stands most of the time and rarely moves their hip through a large enough range of motion to cause relative motion between the user and the exoskeleton. With this insight, exoskeleton hip pivot locations were relocated to better suit the application. By moving the hip pivot of the exoskeleton in front of the user's hip pivot, the counterweight required to balance the tool is reduced. Examples of an exoskeleton with a hip pivot placed at a similar location in the sagittal plane to the hip pivot of the user, and an exoskeleton with a hip pivot placed forward relative to that of the user, are shown in FIGS. 2a and 2b, verses FIGS. 2c and 2d respectively.

Figure 2A:
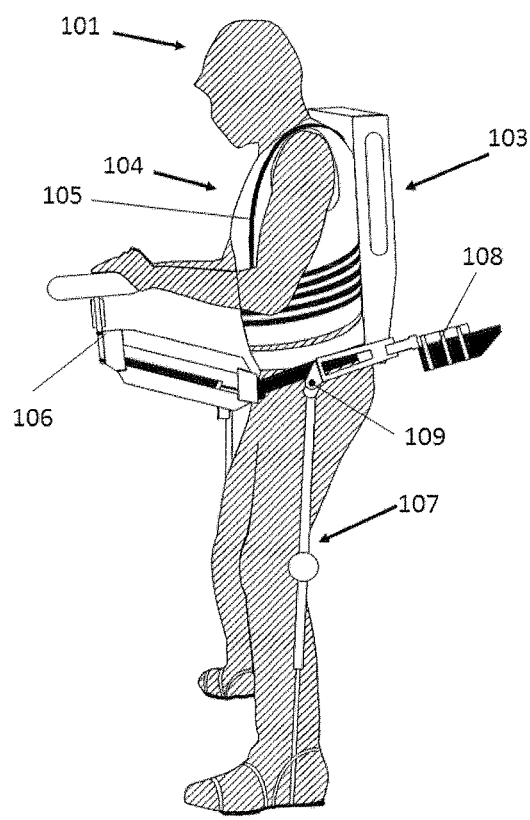
FIG. 2a is a schematic side view of a worker wearing a tool-holding exoskeleton.

More specifically, with reference to FIG. 2a, worker 101 is wearing commercial exoskeleton 103, which is attached to torso 104 of worker 101 by person-exoskeleton strapping 105. Commercial exoskeleton 103 is equipped with tool holding arm 106. The weight of tool holding arm 106 is transferred to commercial exoskeleton 103 which is supported by exoskeleton legs 107 that are connected to exoskeleton 103 by hip pivot 109. As the weight of tool holding arm 106 shifts the balance of exoskeleton 103 forward, exerting a forward torque on hip pivot 109, exoskeleton 103 is equipped with counterweight 108, which exerts a rearward torque on hip pivot 109 in order to counteract the forward torque on hip pivot 109.

Figure 2B:
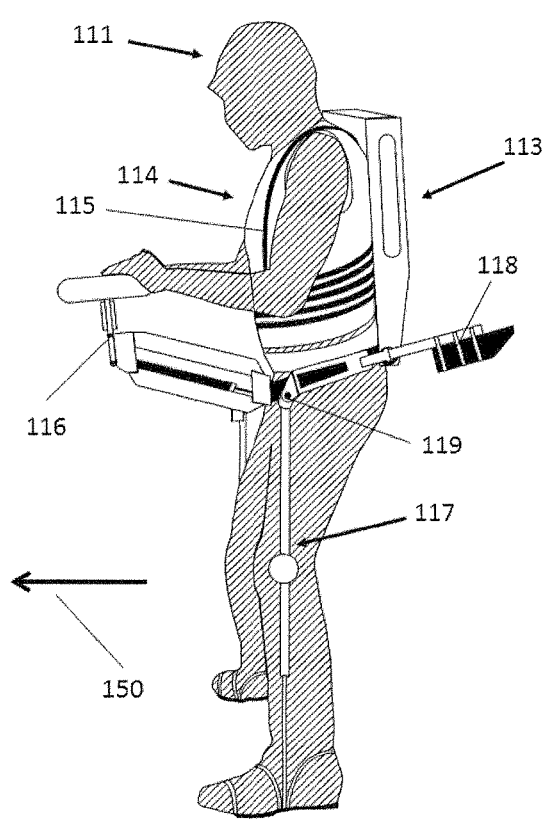
FIG. 2b is a drawing representing a first embodiment that shows a schematic side view of a worker wearing a tool-holding exoskeleton, with the exoskeleton having forward-shifted hips.

With reference to FIG. 2b, worker 111 is wearing a commercial exoskeleton 113, which is attached to torso 114 of worker 111 by person-exoskeleton strapping 115. Exoskeleton 113 is equipped with tool holding arm 116. The weight of tool holding arm 116 is transferred to exoskeleton 113 which is supported by exoskeleton legs 117 that are connected to exoskeleton 113 by forward-shifted hip pivot 119. Arrow 150 indicates the forward direction in the sagittal plane generally referred to in the application as "forward". As the weight of tool holding arm 116 shifts the balance of exoskeleton 113 forward, exerting a forward torque on hip pivot 119, exoskeleton 113 is equipped with counterweight 118, which exerts a rearward torque on forward-shifted hip pivot 119 in order to counteract the forward torque forward-shifted hip pivot 119.

With reference to FIG. 2c, worker 101 is wearing commercial exoskeleton 103, with both the hip pivot of worker 101 and exoskeleton 103 being co-located in the sagittal plane. The torque about hip pivot 109 of exoskeleton 103 due to the tool arm weight and load is created by the force 121 and the lever arm 122. From testing, it has been found that worker 101 generally applies a negligible force to the load, instead generally stabilizing it with their hands; therefore it is reasonable to assume that they apply no force to the load or tool arm. The counterweight torque also acts about hip pivot 109 of exoskeleton 103. The counterweight torque is created by force 124 due to gravity upon the counterweight 108 acting over lever arm 125. Reaction force 126 of leg 107 acts at hip pivot 109. If counterweight 108 is chosen to perfectly balance the given load at a given lever arm 122, then the static balance may be written as:

$$F_{121} \times L_{122} = F_{124} \times L_{125} \quad (1)$$

Where $F_{xxx}$ indicates force xxx and $L_{yyy}$ indicates lever arm length yyy.

With reference to FIG. 2d, worker 111 is wearing commercial exoskeleton 113, with the hip pivot of worker 111 being located at worker hip pivot 133, and hip pivot 119 of exoskeleton 113 being located forward of worker hip pivot 133 by distance 137. The torque about hip pivot 119 of exoskeleton 113 due to the tool arm weight is created by force 131 and lever arm 132 less distance 137. The counterweight torque also about hip pivot 119 of exoskeleton 103 is created by force 134 due to gravity upon counterweight 118 and lever arm 135 plus distance 137. Reaction force 123 of leg 117 acts at hip pivot 119 of exoskeleton 103 offset by hip offset distance 137 from worker hip pivot 133. If counterweight 124 is chosen to perfectly balance the given load at a given lever arm 122, then the static balance may be written as:

$$F_{131} \times (L_{132} - L_{137}) = F_{134} \times (L_{135} + L_{137}) \quad (2)$$

Where $F_{xxx}$ indicates force xxx and $L_{yyy}$ indicates lever arm length yyy.

For the case where the configuration of the tool arm is generally the same as in FIG. 2c, i.e., when $F_{131} = F_{121}$, $L_{132} = L_{122}$, $L_{125} = L_{135}$, then $F_{134}$ may be substantially reduced and the mass of counterweight 124 may be substantially reduced as well, thereby reducing both the overall exoskeleton weight and the force on exoskeleton leg 117. Or, depending on the design, the length of the counterweight lever arm 135 may be substantially reduced, making commercial exoskeleton 113 more maneuverable. In some embodiments, according to the goals of the design, the mass of the counterweight and length of the counterweight lever arm may both be somewhat reduced.

As described in above and shown in FIGS. 2a, 2b, 2c, and 2d, a forward shift in the exoskeleton hip pivot location in the sagittal plane relative to the hip pivot of the person wearing the exoskeleton results in a tool holding exoskeleton with reduced forward hip torque as a result of tool weight. For example, if the hip pivot were moved as far forward as the tool then no counterweight would be required, although in most embodiments this would result in an impractical amount of relative motion between the exoskeleton and the exoskeleton wearer even over small ranges of motion. The location of the hip pivot is selected to maintain enough exoskeleton wearer flexibility for the given task and control relative motion between the exoskeleton wearer's body and the device while requiring an acceptable counterweight torque.

Figure 2E:
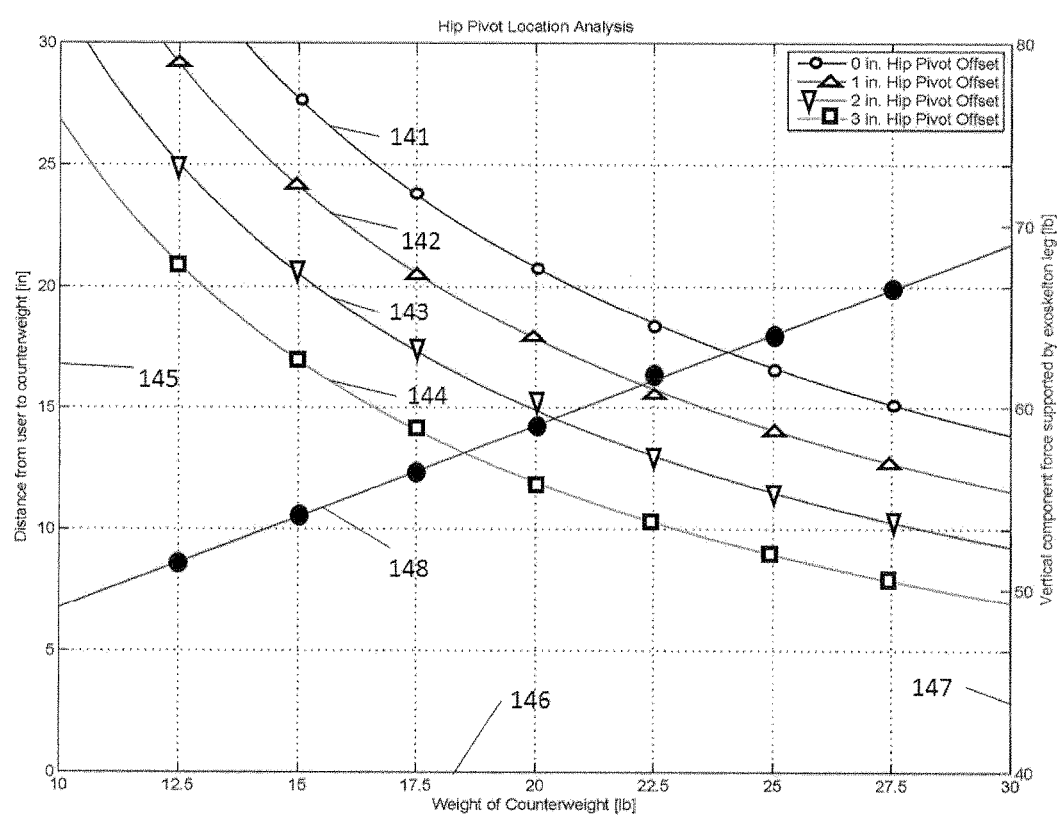
FIG. 2e is a plot showing the calculated counterweight distance and weight required for various hip pivot locations as shown in FIGS. 2c and 2d.

By moving the hip pivot forward, the counterweight torque required is decreased by reducing the distance from the exoskeleton hip pivot to the tool by the amount of the hip offset (hip offset 137 in FIG. 2d). The torque on the user due to the tool weight is reduced which allows the counterweight torque to be reduced without increasing load on the exoskeleton user. The counterweight torque can be reduced by reducing the distance between the weight and the user or reducing the mass used. FIG. 2e shows the relationship between counterweight distances versus counterweight mass for various hip pivot locations. For this plot, the weight of the tool is 25 lbs and the weight of the arm positioning the tool is 14 lbs, although the analysis holds in general. Line 141 with open circle symbols represents the weight versus distance relationship for an exoskeleton designed with the hip pivot aligned with the user's hip pivot, y-axis 145 representing the distance from the exoskeleton wearer to the counterweight, and x axis 146 representing the weight of the counterweight. As the hip offset is increased the curve shifts toward less weight and less distance required; an exoskeleton with a 1-inch hip offset shown by the line 142 with open triangle symbols, an exoskeleton with a 2-inch hip offset shown by the line 143 with open inverted triangle symbols, and an exoskeleton with a 3-inch hip offset shown by the line 144 with open square symbols. Given a fixed distance from the exoskeleton user to the counterweight, the amount of counterweight required decreases as the hip pivot offset distance increases. Likewise, given a fixed amount of counterweight, the distance from the exoskeleton user to the counterweight required decreases as the hip pivot offset distance increases. Also shown in FIG. 2e is line 148, which is marked with black closed circle symbols, that plots the increasing vertical component force supported by the exoskeleton leg on y-axis 147 as the weight of the counterweight increases along x-axis 146.

An exoskeleton designed for a specific tool holding task can greatly benefit from this forward mounted hip pivot design. The forward mounted hip pivot increases the user's mobility by reducing the distance that the counterweight protrudes from the user. In a confined space any increase to the user's size is undesirable. Other benefits include reduced counterweight mass which reduces user fatigue while walking in the device. In the case of an exoskeleton with actuated hips, forward mounted hip pivots result in reduced power consumption due lessened exoskeleton hip actuator torque input.

In one example of a main embodiment, if a tool holding exoskeleton were designed for use in confined spaces, at a given counterweight weight, the distance of the counterweight from the exoskeleton user could be reduced. Based on the plot shown in FIG. 2e, an exoskeleton with a 27.5 pound counterweight and no hip offset would require a 15 inch distance from the exoskeleton wearer to the counterweight, while an exoskeleton with an identical 27.5 pound counterweight but with a 3 inch hip offset would only require a 8 inch distance from the exoskeleton wearer to the counterweight. This shorter counterweight different would be a significant advantage in maneuvering the exoskeleton in confined spaces.

A second embodiment of this invention comprises of an exoskeleton device with a mechanical design that misaligns the exoskeleton hip pivot rearward in the sagittal plane relative to the exoskeleton wearer's hip pivot. For the application of a backpack load bearing exoskeleton, this mechanical design reduces the counter torque required to hold a load in place for the same reason that the hip pivot should be placed in front of the user when the load is in front of the user: the user will be able to adopt a more upright position when the exoskeleton pivot is placed close to the center of mass of the load that it is accepting. This class of non-anthropomorphic hip locations for exoskeletons is based on an insight about the nature of the hip joint in humans: the hip joint is generally placed in line with the center of mass of the load that the hip joint is bearing so that no torque is required about the hip. Just as in the earlier embodiments, where it may not be practical to place the hip pivot directly in line with the load, simply moving it as close as is practically feasible is sufficient to have a beneficial effect. It is important to note that in these embodiments, the weight of the person is transmitted to the ground without the exoskeleton, i.e., the exoskeleton is not bearing the body weight of the person through the exoskeleton hip pivot. If, however, the person is connected tightly to the trunk of the exoskeleton so that the body weight of the person is transferred to the exoskeleton and through the exoskeleton hip pivot, then the ideal exoskeleton pivot location will be at the combined center of mass of the exoskeleton torso, human torso, and load. A representation of a load bearing exoskeleton with rearward shifted hips in shown in FIGS. 3a and 3b.

Figure 3A:
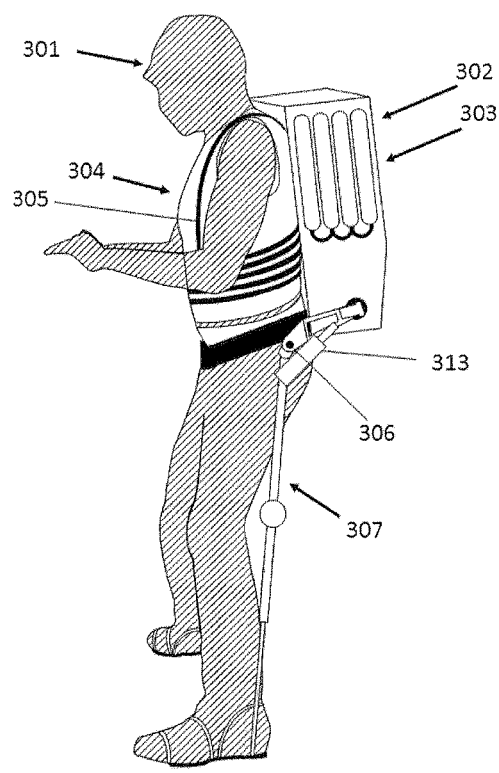
FIG. 3a is a drawing representing a second embodiment that shows a side view of a person wearing an exoskeleton with a load-bearing backpack, with the hips of this exoskeleton being shifted rearward relative to the hips of the exoskeleton wearer.
Figure 3B:
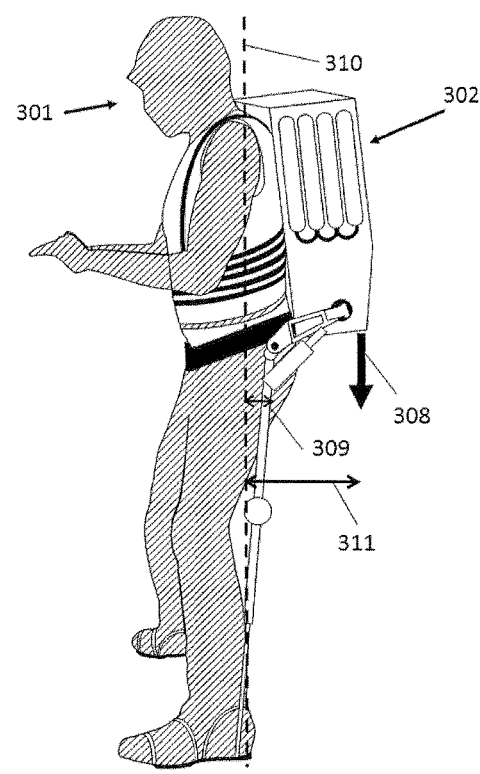
FIG. 3b is drawing representing the second embodiment that shows a side view of a person wearing an exoskeleton with a load-bearing backpack, with the hips of this exoskeleton being shifted rearward relative to the hips of the exoskeleton wearer, showing the forces exerted by the backpack and ground, as well as the distances between the backpack downward force and the hip of the exoskeleton wearer and the offset from the hip of exoskeleton to the hip of the exoskeleton wearer.

With reference to FIGS. 3a and 3b, worker 301 is wearing a commercial exoskeleton 302 which is attached to the torso 304 of worker 301 by person-exoskeleton strapping 305. Commercial exoskeleton 302 is equipped with load-bearing backpack 303 and hip actuator 313, which is configured to generate torque about reward-shifted hip pivot 306. Reward shifted hip pivot is shifted backward from the hip pivot of worker 301 by distance 309. The weight of load-bearing backpack 303 is transferred to commercial exoskeleton 302 which is supported by exoskeleton legs 307 that are connected to exoskeleton 302 by rearward-shifted hip pivot 306.

With further reference to FIGS. 3a and 3b, worker 301 is wearing commercial exoskeleton 302, with the hip pivot of worker 301 being located in the sagittal plane at dashed line 310, and the commercial exoskeleton 302 hip pivot being located in the sagittal plane rearward of dashed line 310 by distance 309. The torque about hip pivot 306 due to the weight of load-bearing backpack 303 is created by the force due to gravity 308 and the lever arm 311 less distance 309. Because of exoskeleton hip offset distance 309, the torque that must be supplied by actuator 313 to counteract the torque generated by force due to gravity 308 is reduced. In this way, the rearward offset hip pivot of commercial exoskeleton 302 decreases the hip actuator requirements.

In another variation of the second embodiment, if a backpack-type load-bearing commercial exoskeleton were being used to carry heavy items by a worker over a distance, and the exoskeleton did not have any hip actuation (i.e., lacked hip actuator 313), shifting the hip joint location of the load-bearing exoskeleton rearward would allow the person to exert less physical input/energy at resisting the backwards torque caused by the load of the exoskeleton, relative to a similar exoskeleton without rearward-shifted hips. This decrease in sustained effort on the part of the worker in the course of wearing the exoskeleton with rearward shifted hips would allow the worker to carry the same load of weight farther distances, or greater weight a similar distance, or to perform an identical task with decreased fatigue and risk of injury.

In some embodiments powered exoskeletons produce a substantial net torque about the hip pivot. An example of such a device is disclosed in U.S. application Ser. No. 12/468,487 which is incorporated herein by reference. In this device, a large torque is generated about the hip pivot by actuators in the same direction as if there was a rear load on the exoskeleton so that the exoskeleton provides propulsive assistance. As a result, the wearer must lean forward to balance the torque transferred from the exoskeleton torso to the wearer's torso; the torque from the exoskeleton is the combination of the actuator torque and any load, either in front of or behind the exoskeleton. If the typical load condition and actuator torques are known, it is possible to balance the loads about the hip pivot in accordance with the present invention by moving the hip pivot an appropriate distance from the normal anthropomorphic location. Typically, in this embodiment, the pivot would move backwards unless the load on the front of the exoskeleton was quite large.

A third embodiment of this invention comprises of an exoskeleton device with a mechanical design that adjustably alters the exoskeleton hip pivot position in the sagittal plane relative to the position of the exoskeleton wearer's hip pivot. This device, which can either be automatically actuated by the exoskeleton control system or manually adjusted by the exoskeleton wearer, allows for differential hip placement in order to compensate for changing load or actuation conditions. For the application of a tool holding exoskeleton, this mechanical design reduces the counter torque required to hold a tool in place while standing by shifting the hip pivot forward, and increases exoskeleton mobility while walking or maneuvering by shifting the hip pivot rearward. Such an exoskeleton device is shown in FIGS. 4a and 4b.

With reference to FIG. 4a, a worker 401 is wearing a commercial exoskeleton 402, which is attached to torso 403 of worker 401 by person-exoskeleton strapping 404. Commercial exoskeleton 402 is equipped with tool holding arm 405 and counterweight 400. The weight of tool holding arm and load 405 is transferred to commercial exoskeleton 402 which is supported by exoskeleton legs 409 that are connected to exoskeleton 402 by adjustable hip pivot 407. Because the weight of tool holding arm 405 and load 406 shifts the balance of exoskeleton 402 forward, adjustable hip pivot 407 is moved into forward adjustable hip pivot position 408 to balance the torques generated by counterweight 400, and arm 405 and load 415.

In some embodiments, the exoskeleton may automatically move adjustment 406 using an electronic control system, while in other embodiments the person may manually move adjustment device 406. In some embodiments, the pivot may have discrete positions, while in others the position may be continuously adjustable.

With reference to FIG. 4b, worker 401 is wearing commercial exoskeleton 402, which is attached to torso 403 of worker 401 by person-exoskeleton strapping 404. Commercial exoskeleton 402 is equipped with tool holding arm 405, but without any load. The weight of tool holding arm 405 is transferred to commercial exoskeleton 402 which is supported by exoskeleton legs 409 that are connected to exoskeleton 402 by adjustable hip pivot 407. Because the lack of any load shifts the balance of exoskeleton 402 backward, adjustable hip pivot 407 is moved into back adjustable hip pivot position 410 to balance the torques generated by counterweight 400 and arm 405. Of course, in a further, analogous configuration not diagrammed, the position of the hip pivot of the device diagrammed in FIG. 3 could be adjustable in the same way described here, allowing adjustment of the hip position based on the load placed on the back of the device.

By the adjustment of adjustable hip pivot 407, the lever arm lengths in equation 2, discussed earlier, may now be changed. Specifically, with reference back to FIG. 2d and equation 2, $L_{137}$ may be changed to suit the load being carried, allowing the exoskeleton or the person to reduce the torque the person must apply at their hip to balance the load in real time.

Although described with respect to preferred embodiments of the invention, it should be understood that various changes and/or modifications could be made without departing from the spirit of the invention. Certainly, there are many possible ways to change the exoskeleton hip pivot offset relative the hip of the exoskeleton wearer. For example, the pelvic portion of the exoskeleton could have a screw mechanism that allows the wearer to manually adjust the depth of the pelvis (i.e., change the distance from the back of the device to the hip pivot) by turning a handle connected to the screw. Alternatively, the device could automatically adjust this position by powering a motor connected to the screw. In a very simple embodiment, pads of different thickness could be placed between the torso of the user and the back of the exoskeleton so that the relative distance between the exoskeleton and user hip pivots would be changed based on the thickness of the pad.

In one example of this third embodiment, a worker is wearing a tool holding exoskeleton that has adjustable hip pivot positioning. While the worker is operating a heavy tool over a long period of time, the exoskeleton hip pivots are in a forward position, relative to the hips of the worker, in order to reduce forward torque at the hip pivot of the exoskeleton. When the worker is done with this tool use task, the worker flips a switch that engages a motor that changes the adjustable hip pivot rearward into a position that is aligned with the hips of the worker. With the exoskeleton hip pivots in this aligned position the worker is more easily able to maneuver and walk in the exoskeleton, allowing for a repositioning of the tool holding exoskeleton to the next location where tool use is required. When the worker reaches the new location where work is required, the worker again flips the switch, engaging a motor that adjusts the exoskeleton hip pivots into the forward position, a position that is most suitable for extended tool use in terms of exoskeleton balance.

In other embodiments it may be advantageous to have adjustable exoskeleton hips that can be shifted in the sagittal plane both forward or rearward of the hips of the exoskeleton wearer. This would allow for a reduction of either forward or rearward torque, and may be advantageous for exoskeletons that are designed for transient lifting of very heavy frontal loads, such as exoskeletons, which would be likely to have actuated hips, that perform forklift-like heavy object stacking, unstacking, relocation, or loading tasks. These exoskeletons would likely be mounted with very heavy rear counterweights to offset forward hip torque while frontal lifting or load carrying was taking place, and would experience significant rearward torque when the front of the exoskeleton was not loaded. Forward adjustment of the exoskeleton hip pivots while frontally loaded and rearward adjustment of the exoskeleton hip pivots while not loaded would be advantageous in reducing of hip torque and the corresponding exoskeleton actuator power requirement to counteract the hip torque. In any case, the exoskeleton hip pivots are not aligned with the hip pivots of the user over some range of angles between the torso and the leg supports.

In other embodiments, it may be desirable for the hip pivot to be polycentric. Polycentric joints are joints where the joint center moves as the angle between the input and output links move. A simple example well understood in the art is a four bar linkage. It is possible for a four bar linkage to be designed and used as a hip pivot so that the hip pivot is generally in front of the exoskeleton when the exoskeleton wearer is standing vertically, as would be desirable in the first embodiment discussed above, but so that it moves backwards and towards a generally anthropomorphic position as the hip angle becomes much larger, such as when the person sits or squats. This embodiment has the advantage of providing a forward hip pivot during standing, but moving the hip pivot to an anthropomorphic position during large excursions so that the motion between the exoskeleton and the user is not large during these maneuvers. It should be understood that this embodiment could be used in conjunction with the other embodiments disclosed herein, including actuated exoskeletons and exoskeletons where the hip pivot location is adjustable. The details of the polycentric linkage are not disclosed here but, based on this disclosure, one skilled in the art could readily design a linkage that continuously moves the hip pivot between different locations as a function of hip angle to achieve various optimal configurations (i.e., for exoskeletons where the load will be in front, the pivot could move forward during standing; for exoskeletons where the load will be in back, the pivot could move back during standing).

Finally, it should be realized that, in all embodiments, the exoskeleton may bear the weight of the user. Alternately, in all embodiments the exoskeleton might only support the weight of the exoskeleton and tool or load, as preferred for the exoskeleton application. In addition, in all embodiments, the exoskeleton might have one or more actuated joints, including but not limited to the hip and knee joints. These actuated joints may or may not assist in the propulsion of the exoskeleton and the exoskeleton wearer.

The invention claimed is:

1. An exoskeleton configured to be coupled to a user, said exoskeleton comprising:

first and second leg supports configured to be coupled to lower limbs of the user and rest on a support surface during a stance phase; and an exoskeleton torso configured to be coupled to an upper body of the user, said torso being interconnected to each of the first and second leg supports at respective exoskeleton hip pivots to allow for flexion and extension between the first and second leg supports and the exoskeleton torso about respective exoskeleton hip axes, wherein said exoskeleton hip axes are not aligned with and can be selectively positioned relative to hip pivots of the user.

2. The exoskeleton of claim 1, further comprising a load connected to the exoskeleton, wherein said exoskeleton hip axes are shifted with respect to the hip pivots of the user in a direction of the load connected to said exoskeleton.

3. The exoskeleton of claim 2, further comprising a load bearing arm configured to hold the load in front of the user and configured to be coupled to said torso, where said exoskeleton hip axes are shifted forward of the hip pivots of the user.

4. The exoskeleton of claim 2, further comprising a load bearing arm configured to hold a load behind the user and configured to be coupled to said torso, wherein said exoskeleton hip axes are shifted backward of the hip pivots of the user.

5. The exoskeleton of claim 2, wherein said exoskeleton hip pivots are movable with respect to said torso whereby the exoskeleton hip axes may be selectively misaligned with the hip pivots of the user.

6. The exoskeleton of claim 5, wherein the exoskeleton hip axes can be selectively positioned forward or rearward of the hip pivots of the user.

7. The exoskeleton of claim 1, wherein said exoskeleton hip pivots are not aligned with the hip pivots of the user over some range of angles between said torso and said leg supports.

8. The exoskeleton of claim 7, wherein said exoskeleton hip pivots are polycentric.

9. A method of controlling a hip geometry of an exoskeleton including first and second leg supports configured to be coupled to a lower limb of a person and rest on a support surface during a stance phase, and an exoskeleton torso configured to be coupled to an upper body of the person and carry a load, said exoskeleton torso being interconnected to each of the first and second leg supports at respective exoskeleton hip pivots to allow for flexion and extension between the first and second leg supports and the exoskeleton torso about respective hip axes, said method comprising:

varying a position of each of said exoskeleton hip pivots relative to said exoskeleton torso to reduce a torque generated by the load about said exoskeleton hip pivots when said leg supports are resting on said support surface.

10. The method of claim 9, wherein the exoskeleton hip pivots are shifted forward relative to the exoskeleton torso.

11. The method of claim 9, wherein the exoskeleton hip pivots are shifted rearward relative to the exoskeleton torso.

12. The method of claim 9, wherein the exoskeleton hip pivots are automatically shifted relative to the exoskeleton torso.

13. The method of claim 9, wherein the exoskeleton hip pivots are manually forward relative to the exoskeleton torso.

14. The method of claim 9, wherein said exoskeleton hip pivots are shifted so as to not be aligned with hip pivots of a person coupled to the exoskeleton, with the exoskeleton hip pivots being selectively shifted over some range of angles.

15. An exoskeleton configured to be coupled to a user, said exoskeleton comprising:

first and second leg supports configured to be coupled to lower limbs of the user and rest on a support surface during a stance phase; and an exoskeleton torso configured to be coupled to an upper body of the user, said torso being interconnected to each of the first and second leg supports at respective exoskeleton hip pivots to allow for flexion and extension between the first and second leg supports and the exoskeleton torso about respective exoskeleton hip axes, wherein said exoskeleton hip axes are forward of and not aligned with the hip pivots of the user.

16. The exoskeleton of claim 15, further comprising a load connected to the exoskeleton in front of the user, wherein said exoskeleton hip axes are shifted with respect to the hip pivots of the user based on and in a direction of the load connected to said exoskeleton.

17. The exoskeleton of claim 16, further comprising a load bearing arm coupled to said torso and configured to hold the load in front of the user.

18. The exoskeleton of claim 15, wherein said exoskeleton hip pivots are movable with respect to said torso whereby the exoskeleton hip axes may be selectively misaligned with the hip pivots of the user.

19. The exoskeleton of claim 15, wherein said exoskeleton hip pivots are not aligned with the hip pivots of the user over some range of angles between said torso and said leg supports.

20. The exoskeleton of claim 19, wherein said exoskeleton hip pivots are polycentric.

* * * * *